US008998988B2

(12) United States Patent
Phillips et al.

(10) Patent No.: US 8,998,988 B2
(45) Date of Patent: Apr. 7, 2015

(54) BUTTRESS PLATE SYSTEM

(75) Inventors: James Milton Phillips, Star, MS (US); Robbie Dale Dickerman, Plano, TX (US)

(73) Assignee: Spinal USA, Inc., Parsippany, NJ (US)

( * ) Notice: Subject to any disclaimer, the term of this patent is extended or adjusted under 35 U.S.C. 154(b) by 246 days.

(21) Appl. No.: 12/981,193

(22) Filed: Dec. 29, 2010

(65) Prior Publication Data
US 2012/0172987 A1 Jul. 5, 2012

(51) Int. Cl.
*A61F 2/44* (2006.01)
*A61B 17/68* (2006.01)
*A61B 17/80* (2006.01)
*A61B 17/70* (2006.01)

(52) U.S. Cl.
CPC ........... *A61B 17/808* (2013.01); *A61B 17/7059* (2013.01); *A61B 17/809* (2013.01)

(58) Field of Classification Search
CPC ........... A61B 17/7044; A61B 17/7059; A61B 17/7074–17/7082; A61B 17/7065; A61B 17/80–17/808
USPC ......... 606/71, 280, 281, 99; 623/17.11–17.16
See application file for complete search history.

(56) References Cited

U.S. PATENT DOCUMENTS

| 5,683,392 | A | 11/1997 | Richelsoph et al. |
| 6,322,562 | B1 | 11/2001 | Wolter |
| 2001/0020185 | A1* | 9/2001 | Ray ............................ 623/17.11 |
| 2004/0153078 | A1* | 8/2004 | Grinberg ......................... 606/75 |
| 2005/0027293 | A1* | 2/2005 | LeHuec et al. .................. 606/61 |

(Continued)

FOREIGN PATENT DOCUMENTS

| EP | 0551187 A1 | 7/1993 |
| EP | 1323395 A2 | 7/2003 |

OTHER PUBLICATIONS

K2M CAYMAN Plate Systems flyer, believed to have been last updated Apr. 28, 2010, available at http://www.k2m.com/en_us/products/details/22, last visited Jun. 13, 2011.
K2M CAYMAN® Buttress, http://www.k2m.com/en_us/products/details/22, © 2005-2011, last visited Jun. 13, 2011.

(Continued)

*Primary Examiner* — Mary Hoffman
*Assistant Examiner* — Michelle C Eckman
(74) *Attorney, Agent, or Firm* — Knobbe, Martens, Olson & Bear, LLP.

(57) ABSTRACT

Systems, devices and methods are provided for assisting in spinal stabilization. A buttress plate system is provided that can include an intervertebral spacer, a buttress plate, a spinal screw, and an insertion instrument. The buttress plate is configured to extend across at least a part of an intervertebral space to block or prevent an intervertebral spacer from backing out of the intervertebral space when the buttress plate is secured to the spine. The buttress plate includes a curved plate body having an aperture therethrough for receiving a spinal screw. The buttress plate also includes a pair of engagement members in the form of spikes to help stabilize the buttress plate relative to the spine prior to securing the buttress plate to the spine. The buttress plate can be coupled to an insertion instrument that is used to guide the buttress plate to a desired position adjacent the spine. Once in a desired position, a spinal screw can be delivered through the insertion instrument and through the aperture of the buttress plate to secure the buttress plate to the spine. The insertion instrument thus helps to properly position the buttress plate adjacent the spine and to deliver a spinal screw toward the aperture of the buttress plate.

19 Claims, 18 Drawing Sheets

(56) References Cited

U.S. PATENT DOCUMENTS

| | | | |
|---|---|---|---|
| 2005/0101960 A1* | 5/2005 | Fiere et al. | 606/72 |
| 2005/0251257 A1* | 11/2005 | Mitchell et al. | 623/17.11 |
| 2006/0106387 A1* | 5/2006 | Fanger et al. | 606/69 |
| 2006/0122607 A1* | 6/2006 | Kolb | 606/71 |
| 2006/0276897 A1* | 12/2006 | Winslow et al. | 623/17.11 |
| 2007/0016204 A1 | 1/2007 | Martinez et al. | |
| 2008/0161925 A1* | 7/2008 | Brittan et al. | 623/17.16 |
| 2008/0177390 A1* | 7/2008 | Mitchell et al. | 623/17.16 |
| 2009/0036933 A1* | 2/2009 | Dube et al. | 606/282 |
| 2009/0076556 A1* | 3/2009 | McGarity et al. | 606/281 |
| 2009/0088854 A1* | 4/2009 | Strauss | 623/17.16 |
| 2009/0270990 A1* | 10/2009 | Louis et al. | 623/17.16 |
| 2009/0306779 A1* | 12/2009 | Ahn | 623/17.11 |
| 2010/0100131 A1* | 4/2010 | Wallenstein | 606/279 |
| 2010/0106196 A1* | 4/2010 | Erickson et al. | 606/281 |
| 2010/0228852 A1* | 9/2010 | Gemelos et al. | 709/224 |
| 2012/0143336 A1* | 6/2012 | Aflatoon et al. | 623/17.16 |

OTHER PUBLICATIONS

MacroPore, Inc. OS Spinal System, 510(k) Summary of K010911, dated Jul. 20, 2001.

Omni Surgical, LP Black Widow Anterior Buttress Plate, 510(k) Summary of K081770, dated Apr. 2, 2009.

Synthes® Spine Titanium Buttress Locking Plate (BLP) System, believed to be available by 1997, http://us.synthes.com/Products/Spine/Anterior+Stabilization/Titanium+Buttress+Locking+Plate+(BLP)+System.htm, last visited Jun. 13, 2011.

Synthes® Spine Titanium Buttress Locking Plate Technique Guide © 1997, available at http://www.syntheskyo.com/spine_kyo/home/submenu.htm?bp=1, last visited Jun. 13, 2011.

International Search Report and Written Opinion dated Nov. 7, 2012 of PCT/US2011/067436 which is the parent application in 12 pages.

International Preliminary Report on Patentability for PCT Application No. PCT/US2011/067436, dated Jul. 7, 2013.

* cited by examiner

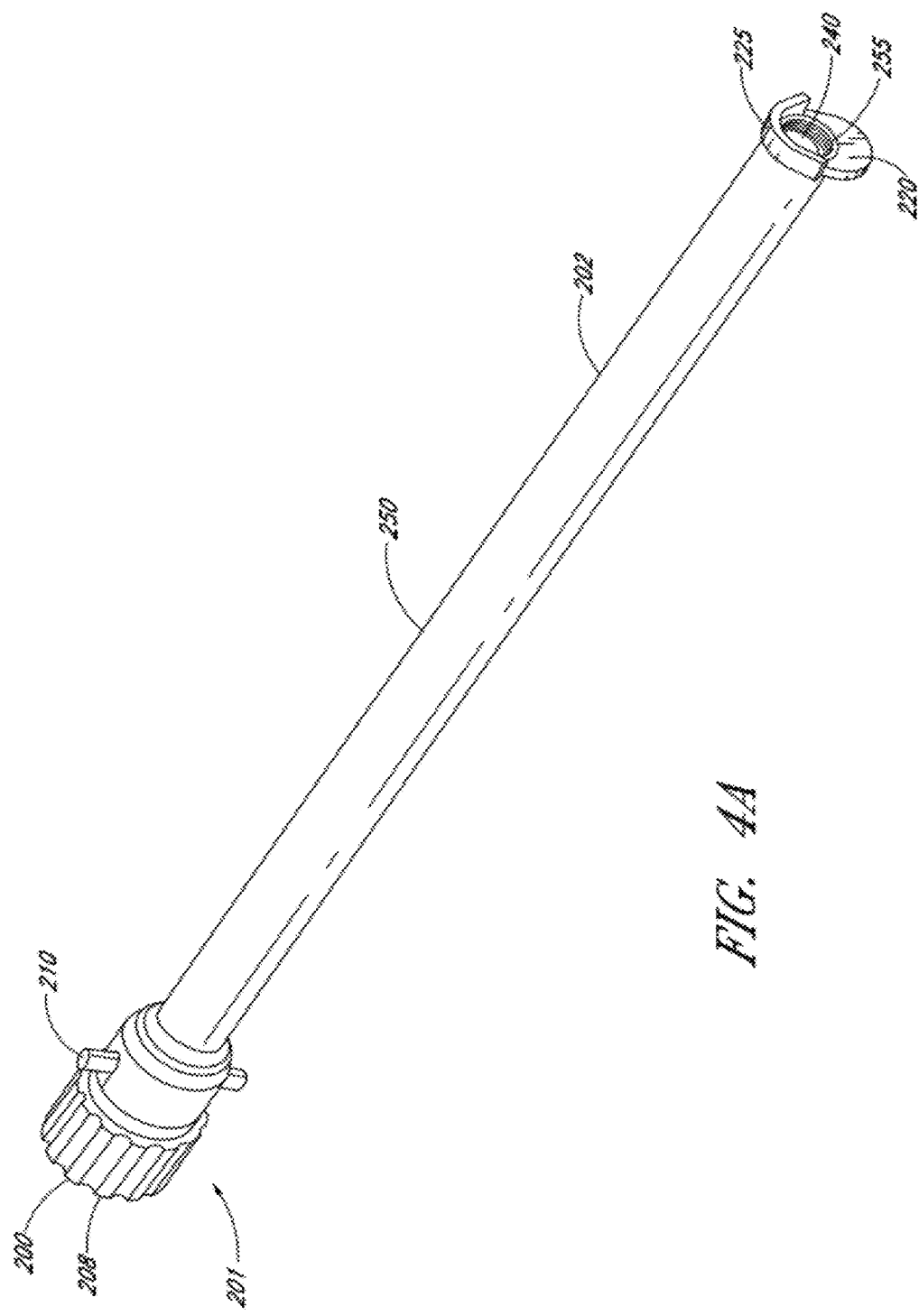

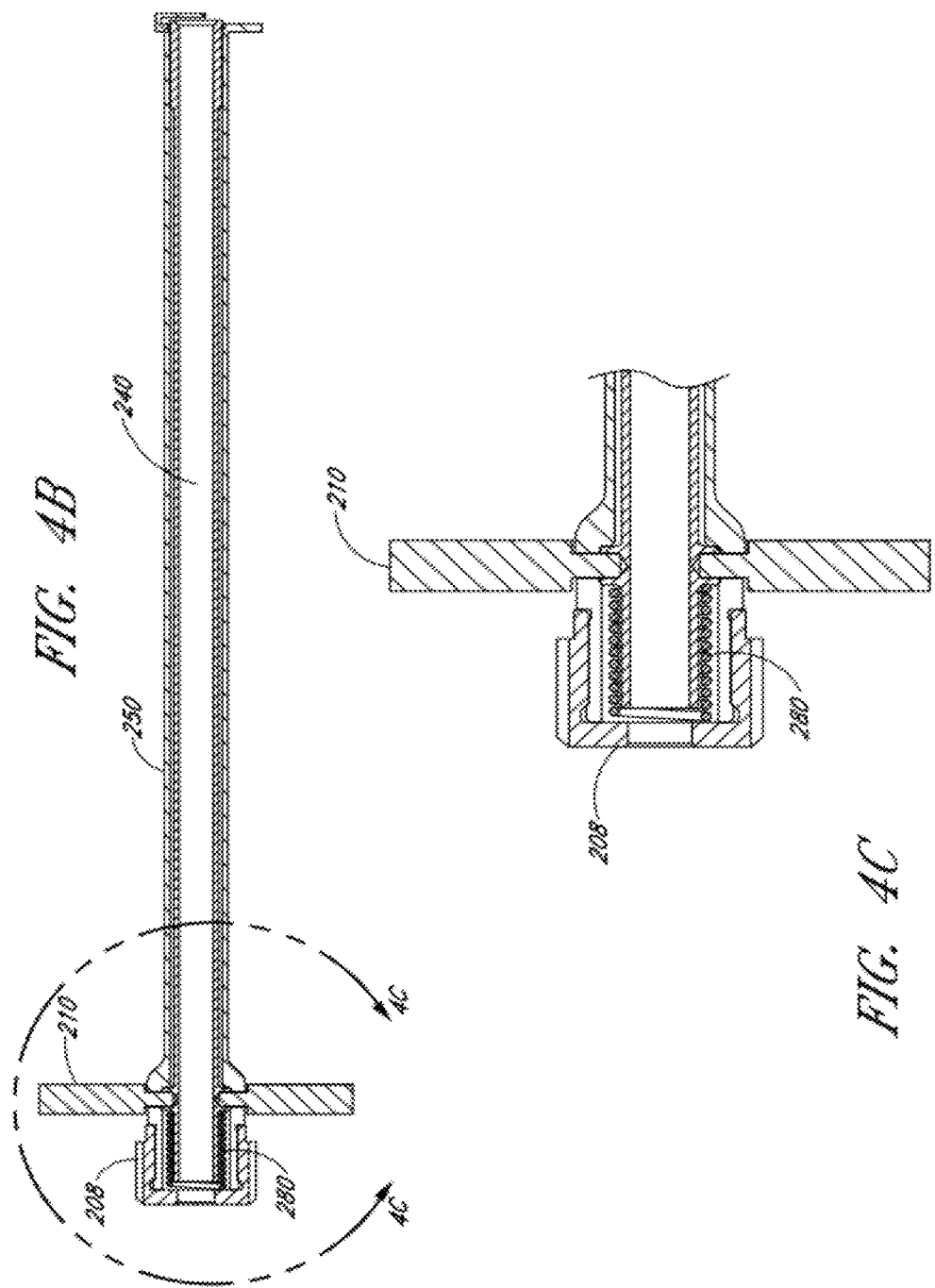

BUTTRESS PLATE SYSTEM

BACKGROUND OF THE INVENTION

1. Field of the Invention

The present application relates to devices, systems and processes for spinal surgeries. In particular, the present application relates to devices, systems and processes for disc replacement surgeries.

2. Description of the Related Art

The spine relies on intervertebral spinal discs in between adjacent vertebrae to serve as mechanical cushions and to transmit compressive loads. Spinal discs are composed of an outer annulus fibrosus that surrounds an inner nucleus pulposus. The annulus fibrosus is composed of laminae of fibrous tissue and fibrocartilage, while the nucleus pulposus is composed of water, chondrocytes, collagen fibrils and proteoglycan aggrecans that have hyaluronic long chains. The nucleus pulposus functions to distribute hydraulic pressure in all directions within each disc under compressive loads.

The nucleus pulposus, which begins early in life as eighty percent water, slowly dessicates with age. This causes the spinal disc to lose its cushioning ability and ability to bear loads, resulting in pain in the back and lower extremities. To resolve these problems, the degenerated nucleus may be removed and replaced. In some other cases, the nucleus may be removed and the vertebrae may be fused together in a spinal fusion procedure, which may include implanting an intervertebral cage and/or bone growth material to facilitate fusion of the vertebrae.

During vertebral disc replacement surgery, it is commonplace to insert an intervertebral spacer between two adjacent vertebrae in the place of a ruptured or diseased disc. Such intervertebral spacers can include, but are not limited to, bone grafts, peek cages, titanium cages, stainless steel cages, bioresorbable cages, and the like. In some circumstances, following implantation, these intervertebral spacers can inadvertently back out or be displaced from an intervertebral space.

There remains a need for devices that can assist in blocking or preventing intervertebral spacers from backing out of an intervertebral space. In addition, there remains a need for instruments that can assist in guiding such devices to a desired location adjacent a spine.

SUMMARY OF SOME EMBODIMENTS

The present application relates to devices, systems and processes for spinal surgeries. In particular, the present application relates to a buttress plate that can be positioned across an intervertebral space to prevent a spacer from unintentionally backing out of an intervertebral space.

In some embodiments, a spinal implant system comprising an intervertebral spacer, buttress plate, screw and insertion instrument is provided. The intervertebral spacer is configured and arranged to be positioned in an intervertebral space between a first vertebra and a second vertebra of a patient. The buttress plate includes a plate body configured and arranged to extend across at least a portion of the intervertebral space to at least inhibit the intervertebral spacer from backing out from the intervertebral space when the buttress plate is connected to at least one vertebra. The buttress plate further includes a top surface and a bottom surface, wherein the bottom surface includes at least one engagement member and a recessed edge and the top surface includes a groove. In addition, an aperture extends through the top surface and bottom surface of the buttress plate. The screw is configured to be inserted through the aperture of the buttress plate and into at least one vertebra to connect the buttress plate to the at least one vertebra. The insertion instrument includes a proximal portion, a distal portion and a sleeve there between, as well as an inner shaft having a lumen disposed within at least a part of the sleeve. The proximal portion includes a cap having a delivery hole and a pin actuator for controlling retraction of the inner shaft within the sleeve, while the distal portion includes a receiver portion configured to receive the buttress plate. The insertion instrument is configured to couple to the buttress plate and guide the screw through the lumen to the aperture of the buttress plate coupled to the insertion instrument.

In some embodiments, a spinal implant system comprising an intervertebral spacer, buttress plate and insertion instrument is provided. The intervertebral space is configured and arranged to be positioned in an intervertebral space between a first vertebra and a second vertebra of a patient. The buttress plate includes a plate body configured and arranged to extend across at least a portion of the intervertebral space and at least inhibit the intervertebral spacer from backing out when the buttress plate is connected to at least one vertebra. The buttress plate further includes an aperture for receiving a screw. The insertion instrument includes a proximal portion, a distal portion and a sleeve there between, wherein the distal portion of the insertion instrument is configured to couple to the buttress plate. The insertion instrument is configured to guide the screw through the sleeve to the aperture of the buttress plate when the buttress plate is coupled to the insertion instrument.

In some embodiments, a spinal implant system comprising a buttress plate and insertion instrument is provided. The buttress plate includes a plate body configured and arranged to extend across at least a portion of the intervertebral space. The buttress plate further includes an aperture for receiving a screw. The insertion instrument includes a proximal portion, a distal portion and a sleeve there between, wherein the distal portion of the insertion instrument is configured to couple to the buttress plate. The insertion instrument is configured to guide the screw through the sleeve to the aperture of the buttress plate when the buttress plate is coupled to the insertion instrument.

In some embodiments, a spinal implant method is provided comprising providing a buttress plate comprising a plate body having an aperture therethrough; coupling the buttress plate to a distal portion of an insertion instrument; using the insertion instrument to guide the buttress plate to a position adjacent a spine; delivering a screw through the insertion instrument and through the aperture of the buttress plate to a vertebral body; and decoupling the buttress plate from the insertion instrument following securing of the buttress plate to the vertebral body.

BRIEF DESCRIPTION OF THE DRAWINGS

FIGS. 4A-4C illustrate different views of a buttress plate insertion instrument according to some embodiments of the present application.

DETAILED DESCRIPTION OF EMBODIMENTS

The present application relates to devices, systems and processes for spinal surgeries. In particular, the present application relates to a buttress plate system that can be used in disc replacement surgeries.

In some embodiments, the buttress plate system comprises an intervertebral spacer, a buttress plate, and a spinal screw. The intervertebral spacer can be configured and arranged to be recessed between two vertebrae of a patient in an intervertebral space. The buttress plate can be positioned adjacent the spine and can be arranged to extend across at least a portion of the intervertebral space to block or prevent the intervertebral spacer from backing out of the intervertebral space. The buttress plate can be securely fixed to one or more vertebrae via one or more spinal screws that are inserted through the buttress plate and into bone member.

In some embodiments, the buttress plate system also includes a buttress plate insertion instrument. The buttress plate can be coupled to the insertion instrument. The insertion instrument can be used to direct the buttress plate to a desired location adjacent a spine. In some embodiments, the insertion instrument can also help guide a spinal screw that will secure the buttress plate to an intervertebral body.

Each of the components of the buttress plate system, including the intervertebral spacer, buttress plate, spinal screw, and insertion tool, are described below. One skilled in the art will appreciate that each component has its own advantageous features and can be used alone or in combination with any of the other components discussed herein.

Buttress Plate

Figure 1:
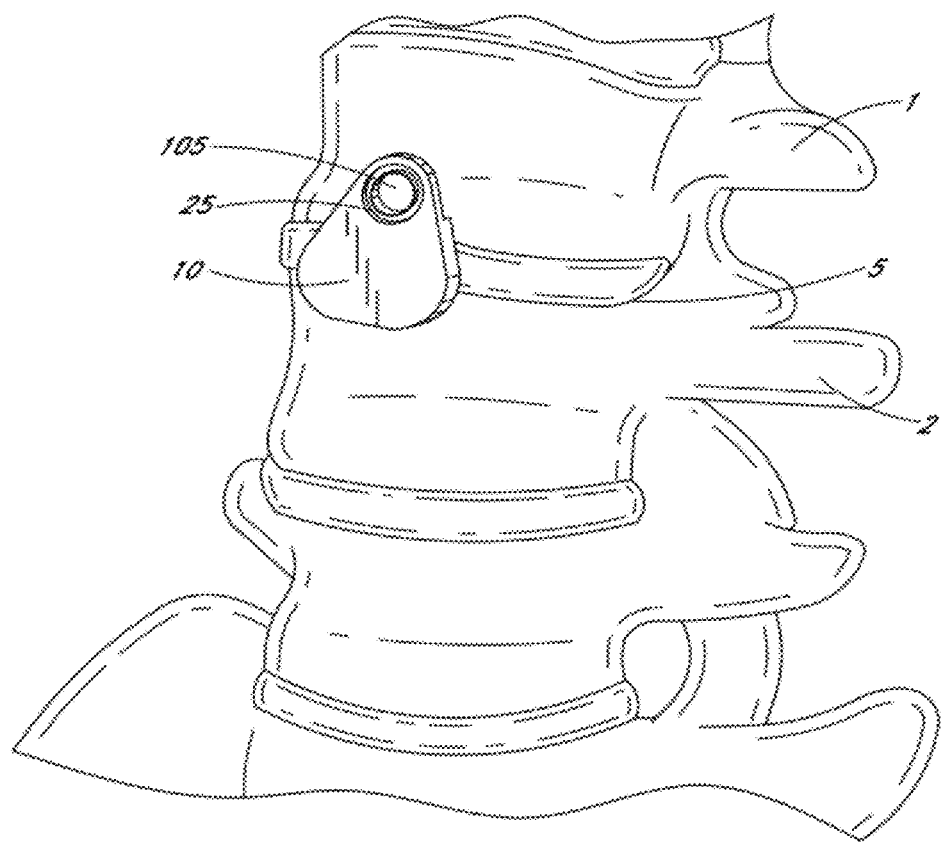
FIG. 1 illustrates a buttress plate positioned across an intervertebral space according to some embodiments of the present application.

FIG. 1 illustrates a buttress plate positioned across an intervertebral space according to some embodiments of the present application. The buttress plate 10 is designed to block or prevent an intervertebral spacer 5 from unintentionally backing out of an intervertebral space between a first vertebra 1 and a second vertebra 2. The buttress plate 10 includes at least one aperture 25 configured to receive a spinal screw 105. The screw 105 can be used to secure the buttress plate 10 to a vertebral member.

Figure 2:
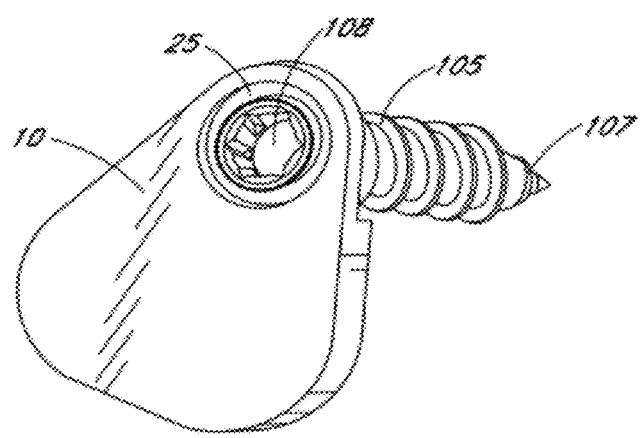
FIG. 2 illustrates a buttress plate system including a buttress plate and spinal screw according to some embodiments of the present application.

FIG. 2 illustrates a buttress plate system according to some embodiments of the present application. The buttress plate system includes a buttress plate 10 having an aperture 25 and a spinal screw 105 having a shaft 107 and head member 108. The aperture 25 extends through the buttress plate 10. In some embodiments, the spinal screw 105 is inserted through the aperture 25 such that only the shaft 107 goes through the aperture while the head 108 rests comfortably within a space formed within the buttress plate 10.

Figure 3A:
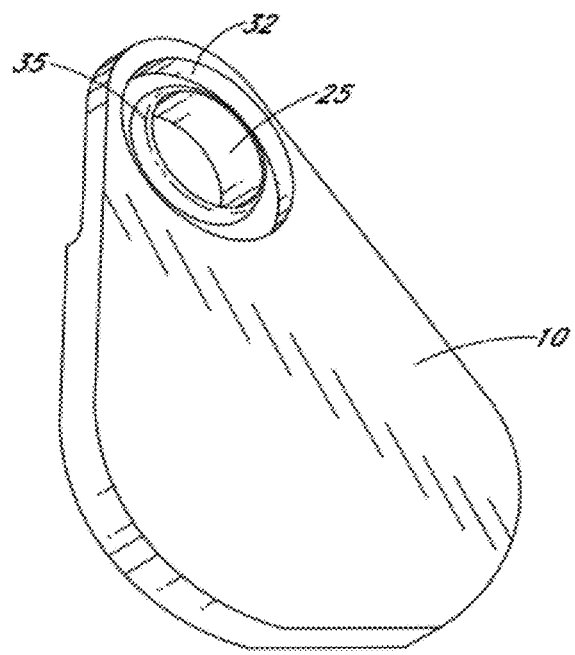
FIGS. 3A-3C illustrate different views of a buttress plate according to some embodiments of the present application.
Figure 3B:
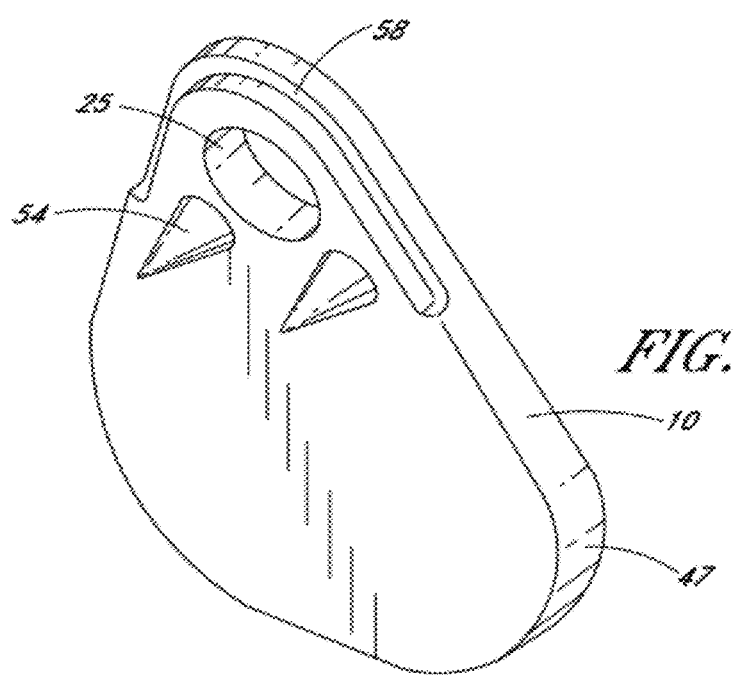
Figure 3C:
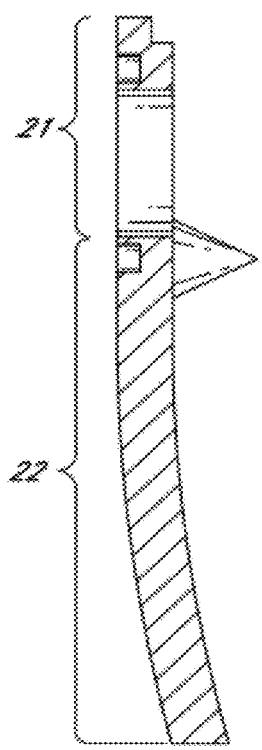

FIGS. 3A-3C illustrate different views of a buttress plate according to some embodiments of the present application. FIG. 3A is a perspective view of a top surface 17 of the buttress plate 10, while FIG. 3B is a perspective view of a bottom surface 47 of the buttress plate 10. FIG. 3C is a side profile of the buttress plate 10.

On its top surface (shown in FIG. 3A), the buttress plate 10 includes a recessed groove 32 that surrounds a flange or ring member 35. On its bottom surface 47 (shown in FIG. 3B), the buttress plate 10 includes engagement members 54 in the form of spikes and a recessed edge 58. The buttress plate 10 further includes an aperture 25 that extends through the top surface 17 and bottom surface 47 of the buttress plate 10. Each of these features will be discussed in more detail below.

The buttress plate 10 is sized and configured to extend across at least a portion of an intervertebral space to block or prevent an intervertebral spacer from unintentional back out. As shown in the figures, the buttress plate 10 includes a plate body 20 having a top surface 17 and bottom surface 47 that are substantially smooth. In the illustrated embodiments, the plate body 20 is substantially triangular in shape and advantageously does not have any pointed edges or corners that could inadvertently damage adjacent tissue. Rather, the edges of the buttress plate 10 are substantially smooth, and the corners of the triangular plate body 20 are substantially rounded. While having a triangular plate body 20 provides advantages over conventional buttresses by providing a design with a reduced number of edges, thereby reducing the risk of damage to adjacent tissue, one skilled in the art will appreciate that plate bodies of different shapes can also be used, including rectangular, square or circular.

FIG. 3A illustrates a perspective view of a top surface 17 of the buttress plate 10. When the buttress plate 10 is attached to a vertebral body, the top surface 17 of the buttress plate 10 faces outward from the spine and is exposed. The top surface 17 of the buttress plate is substantially smooth to reduce the risk of damage to tissue that is placed in contact with the buttress plate 10.

As shown in FIG. 3A, the buttress plate 10 includes an aperture 25 through which a spinal screw 105 can be inserted to secure the buttress plate 10 to a vertebral body. In some embodiments, the aperture is sized and configured to receive a shaft 107 of a spinal screw 105 therethrough, but not the head 108 of the spinal screw 105. In some embodiments, the aperture can have a radius of between 0.2 cm to 1.5 cm. The aperture 25 is surrounded and formed in part by a ring member 35 that is adjacent to a recessed groove 32.

The buttress plate 10 includes a single aperture 25 through which a spinal screw 105 can be inserted and advantageously, only one screw need be inserted through the buttress plate 10 and through the vertebral body to secure the buttress plate to the spine. This reduces the amount of trauma to the spine that can occur when more than one spinal screw is inserted into two or more vertebral bodies. One skilled in the art will appreciate, however, that other embodiments of the buttress plate 10 can include two or more apertures for the delivery of additional screws, which may also have advantages, such as increased coupling of the buttress plate to the spine. Accordingly, the buttress plate 10 can include one, two, three, four or more apertures for spinal screw delivery.

Located around the ring member 35 is a recessed groove 32. Although the recessed groove 32 is circular in shape, grooves of other shapes (e.g., square or rectangular) are also possible. The recessed groove 32 is advantageously configured to receive a spring-loaded inner shaft 255 of an insertion instrument 200 (shown in FIG. 4A) to secure the buttress plate 10 to the insertion instrument 200. In some embodiments, the buttress plate 10 is secured to the insertion instrument 200 outside of a body in preparation for a surgical procedure. Once the buttress plate 10 is secured to the insertion instrument 200, the insertion instrument 10 can deliver the buttress plate 10 to a location adjacent to the spine as part of a minimally invasive, mini-open or open surgical procedure. Once in a desired location, the buttress plate 10 can be stabilized by using the engagement members 54 to engage an exterior portion of a vertebral body. Once in a stabilized position, the buttress plate 10 can be fixed to the vertebral body by inserting a spinal screw 105 through the aperture 25. Once the spinal screw 105 is inserted through the aperture 25 and into a vertebral body, the inner shaft of the insertion instrument 200 can then be retracted from the recessed groove 32 of the buttress plate 10 (as discussed in more detail below), thereby decoupling the insertion instrument from the buttress plate. The insertion instrument can then be removed from the body while the buttress plate 10 is left in place, fixed against a vertebral body.

FIG. 3B is a perspective view of a bottom surface 47 of the buttress plate 10. When the buttress plate 10 is attached to the spine, the bottom surface 47 of the buttress plate 10 faces toward the spine. Like the top surface 17, the bottom surface 47 of the buttress plate is substantially smooth to reduce the risk of damage to tissue that is placed in contact with the buttress plate 10.

As shown in FIG. 3B, the aperture 25 of the buttress plate 10 extends from the top surface 17 to the bottom surface 47 of the buttress plate. On the bottom surface 47 of the buttress plate 10 are a pair of engagement members 54 in the form of spikes. One purpose of the engagement members 54 is to help stabilize the buttress plate 10 relative to the spine when it is positioned adjacent to the spine, but not yet affixed to the spine by a spinal screw 105. The engagement members 54 advantageously dig into or engage a portion of a vertebral body, thereby helping to stabilize the buttress plate 10 while the spinal screw 105 is inserted through the aperture 25 and into the spine. While the engagement members 54 are in the form of pointed spikes to assist in engagement with the spine, the engagement members 54 can also be less pointed (e.g., square or rounded peg members).

As shown in FIG. 3B, the bottom surface 47 of the buttress plate 10 also includes a recessed edge 58 that is formed along an edge near the aperture 25. The recessed edge 58 is configured to allow an insertion instrument (shown in FIG. 4A) to engage and secure the buttress plate 10 in order to facilitate delivery of the buttress plate 10 to a location adjacent a spine, as will be discussed further below. In other embodiments, the buttress plate 10 can be held at locations other than the recessed edge 58 to facilitate delivery of the buttress plate 10 to a particular location.

FIG. 3C illustrates a side profile of the buttress plate 10. While in some embodiments, the buttress plate 10 is substantially flat, in other embodiments, the buttress plate 10 includes some curvature. As shown in FIG. 3C, the buttress plate 10 can have a substantially flat upper portion 21 that curves as it extends toward a lower portion 22. In some embodiments, the degree of curvature between an upper portion 21 and a lower portion 22 can be between 0 and 30 degrees. Advantageously, the curvature helps the buttress plate 10 to better conform to the natural shape of the human spine.

Insertion Instrument

In some embodiments, the buttress plate can be delivered to a desired location within a body using an insertion instrument as described herein. Advantageously, the insertion instrument can also serve to guide a spinal screw toward a buttress plate aperture. The spinal screw can then be inserted through the buttress plate to secure the buttress plate to a spine. The insertion instrument can also advantageously serve as a cover for the spinal screw or other implantation tools that are delivered through the insertion instrument, thereby reducing the risk of damage to tissue that could otherwise come into contact with the screw or tools.

FIGS. 4A-4C illustrate different views of a buttress plate insertion instrument according to embodiments of the present application. FIG. 4A illustrates a perspective view of the insertion instrument, while FIGS. 4B and 4C illustrate different cross-sectional views of the insertion instrument.

As shown in FIG. 4A, the insertion instrument 200 includes a proximal portion 201, a distal portion 202 and a sleeve 250 having an inner lumen therethrough. Within the sleeve 250 is an inner shaft 255 having a distal end that can extend beyond the distal end of the sleeve 250. The proximal portion 201 of the insertion instrument 200 includes a handle portion 205, a cap 208 and a pin actuator 210. The distal portion 202 of the insertion instrument 200 includes a buttress end 220 and receiving portion 225. Each of these features is discussed in more detail below.

The insertion instrument 200 includes a sleeve 250 having a lumen therethrough. The sleeve 250 can be sized and configured to receive an inner shaft 255 therein, as well as one or more spinal implants and implantation tools.

An inner shaft 255 can be received within the sleeve 250 of the insertion instrument 200. Like the sleeve 250, the inner shaft 255 includes a lumen 240. In some embodiments, a spinal screw 105 (shown in FIG. 2) can pass through the lumen of the inner shaft 255 and be directed through the aperture 25 of a buttress plate 10. Spinal tools (e.g., screw driver, awl) or portions thereof (e.g., screw driver shaft) can also be delivered through the inner shaft 255. For example, a spinal screw can be delivered through the inner shaft lumen 240 and into the aperture 25 of a buttress plate 10 attached to the insertion instrument 200. The shaft of a screw driver can then be delivered through the inner shaft lumen 240 to interact with a head portion of the spinal screw to secure the spinal screw to a vertebral body.

Advantageously, the inner shaft 255 and outer sleeve 250 serve as guides for the delivery of a spinal screw 105 to the aperture 25 of a buttress plate 10 when the buttress plate 10 is attached to the insertion instrument 200. In addition, the inner shaft 255 and outer sleeve 250 also serve as protective coverings over the one or more spinal screws and tools that are delivered through their lumens, thereby advantageously preventing tissue damage that could be caused by tissue contacting the screws and tools (which may have sharp, rough or abrasive edges) if delivered without a protective covering.

Figure 5A:
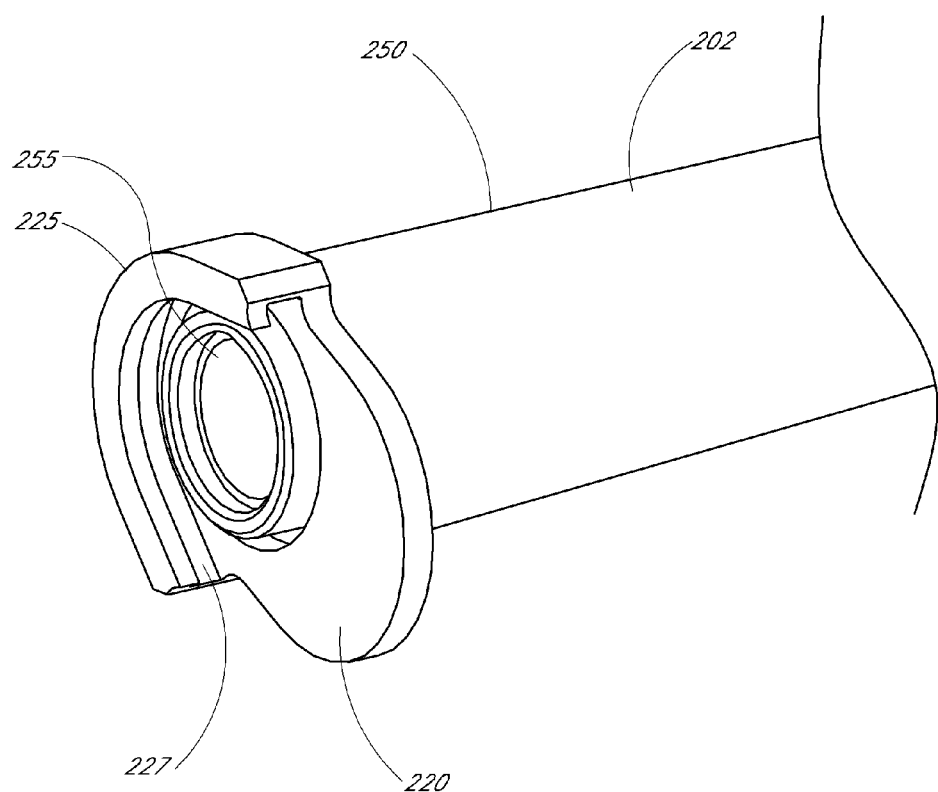
FIGS. 5A-5D illustrate different views of a distal portion of an insertion instrument according to some embodiments of the present application.

In some embodiments, the inner shaft 255 is configured such that it extends beyond a distal end of the sleeve 250 and even beyond an upper surface of the buttress end 220 (as shown in FIG. 5A). When the inner shaft 255 is in this position, the inner shaft 255 can be considered to be in "extended mode." The inner shaft 255 is also configured such that it is substantially or completely retractable within the sleeve 250, whereby it does not extend beyond the distal end of the sleeve 250 and/or surface of the buttress end 220. When the inner shaft 255 is in this position, the inner shaft 255 can be considered to be in "retracted mode." The retraction of the inner shaft 255 can be controlled by the pin actuator 210 and spring member 280 as discussed further below.

In some embodiments, the insertion instrument 10 is configured such that its "normal mode" is its extended mode. In these embodiments, force can be applied to the pin actuator 210 (e.g., the pin actuator 210 can be pulled or pushed by hand as in FIG. 6C) to retract the inner shaft 255. Upon releasing the force on the pin actuator 210, the inner shaft 255 can return back to its original, extended position.

If a buttress plate 10 is not yet attached to the insertion instrument 10, retraction of the inner shaft 255 into the sleeve 250 provides a space for which the buttress plate 10 can be placed on the distal portion of the sleeve 250. If a buttress plate 10 is already attached to the insertion instrument 10, retraction of the inner shaft 255 into the sleeve 250 can release and decouple the buttress plate 10 from the insertion instrument.

Figure 5B:
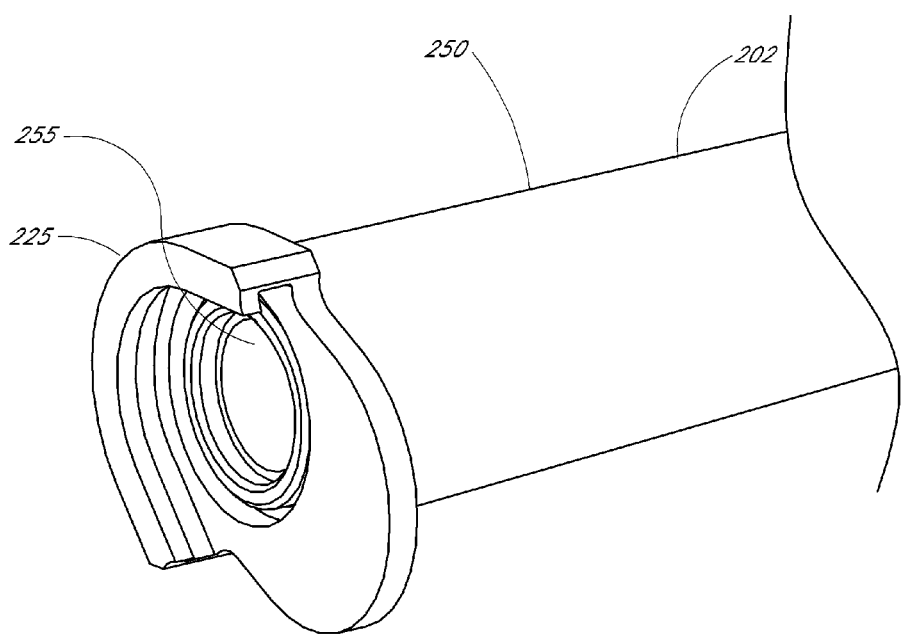
Figure 5C:
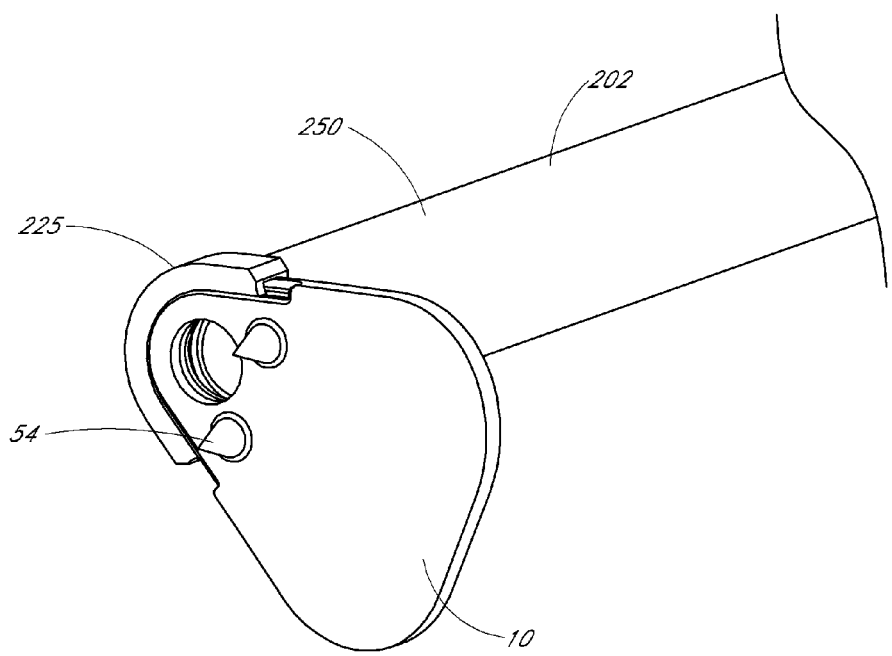
Figure 5D:
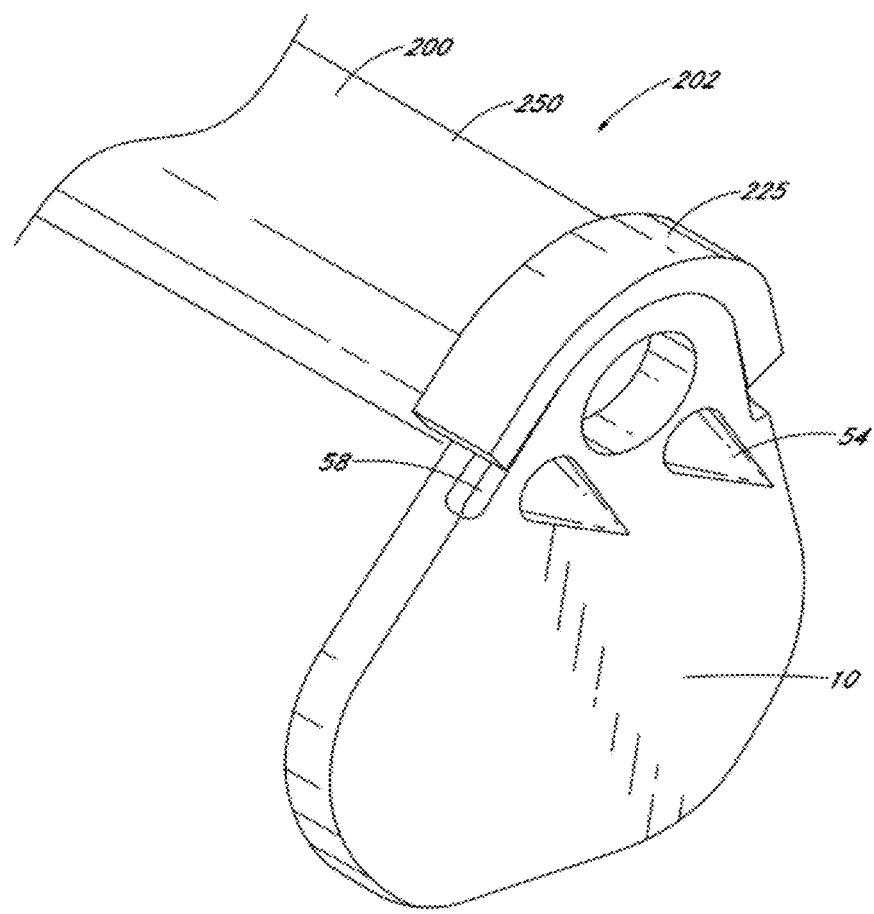

FIGS. 5A-5D illustrate different views of a distal portion of an insertion instrument according to some embodiments of the present application. FIGS. 5A and 5B illustrate a distal portion 202 of the insertion instrument 200 in an extended and retracted position. FIGS. 5C and 5D illustrate a distal portion 202 of the insertion instrument 200 following retraction of the inner sleeve 255 and insertion of a buttress plate 10 therein.

As shown in FIG. 5A, the distal portion 202 of the insertion instrument 200 includes a buttress end 220 and receiver portion 225. The buttress end 220 comprises a substantially flat or planar member. The receiver portion 225 comprises a curvilinear member having a recess 227 formed therein. In some embodiments, the buttress end 220 and receiver portion 225 are formed from a monolithic piece, while in other embodiments, the buttress end 220 and receiver portion 225 are formed separately and attached to one another. In FIG. 5A, the inner shaft 255 is in an extended position beyond the distal end of sleeve 250 and no buttress plate 10 is coupled to the distal portion 202.

FIG. 5B illustrates the distal portion 202 of the insertion instrument 200 with the inner shaft 255 retracted. In this position, a buttress plate 10 can be delivered and securely coupled to the insertion instrument 200. A buttress plate 10 can be positioned in contact with the distal portion 202 of the insertion instrument, such that a top surface 17 of the buttress plate 10 rests against the buttress end 220 while its recessed edges can matingly fit within the recess 227 formed in the receiver portion 225 of the insertion instrument 200, as shown in FIGS. 5C and 5D. To secure the buttress plate 10 to the insertion instrument 200, the inner shaft 255 can be re-extended (e.g., by releasing the force on the pin actuator) such that the distal end of the inner shaft 255 is inserted into the groove 32 (shown in FIG. 3A) of the buttress plate. The re-extended inner shaft 255 can advantageously compress the buttress plate 10 against the surface of the buttress end 220 to secure the buttress plate 10 to the insertion instrument 200.

Figure 6A:
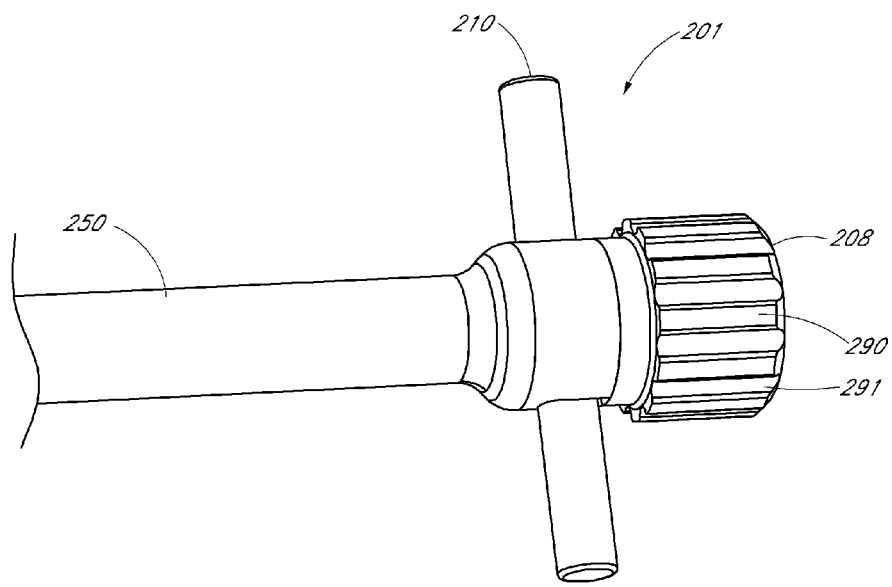
FIGS. 6A-6C illustrate different views of a proximal portion of an insertion instrument according to some embodiments of the present application.
Figure 6B:
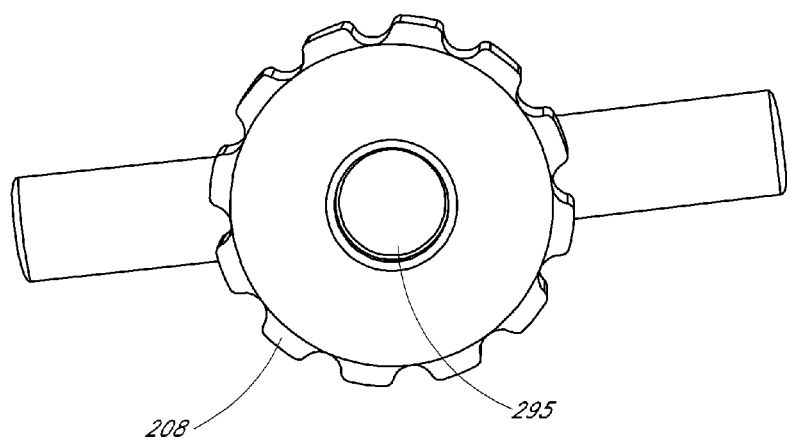
Figure 6C:
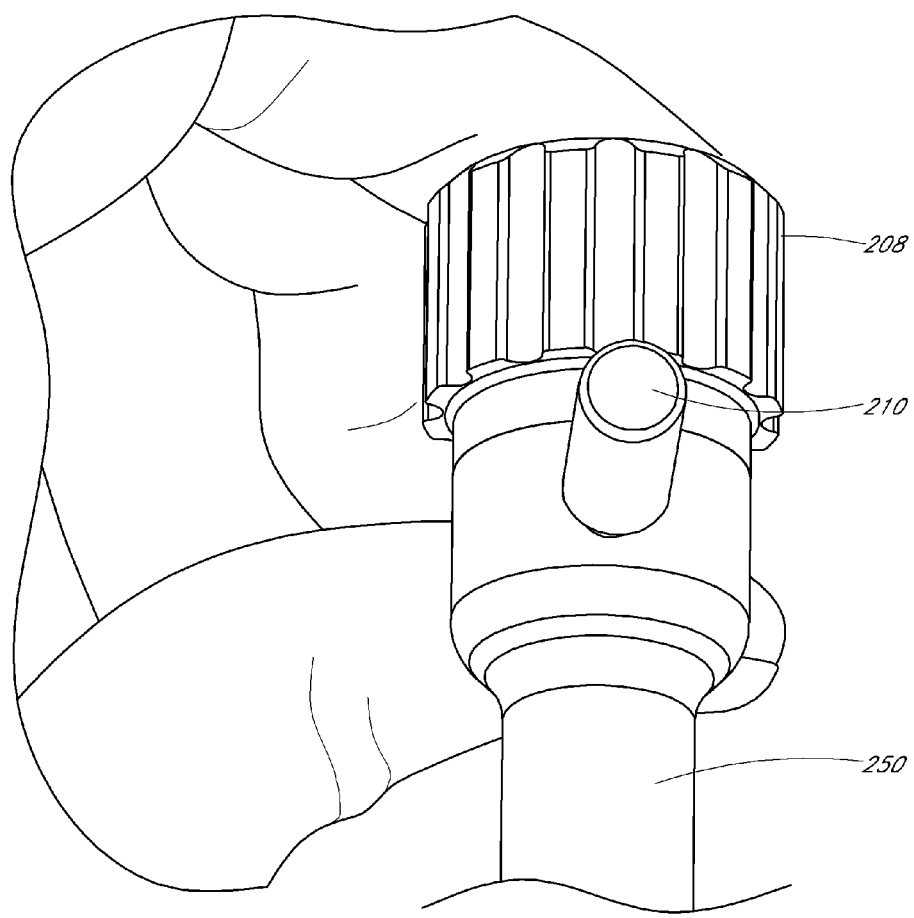

FIGS. 6A-6C illustrate different views of a proximal portion of an insertion instrument according to embodiments of the present application. As shown in FIG. 6A, the proximal portion 210 of the insertion instrument 200 includes a handle portion 205, cap 208, and pin actuator 210. The handle portion 205 can comprise portions of the sleeve 250 and/or the cap 208. A user can hold the handle portion 205 to navigate and steer the insertion instrument 200 within a human body.

The cap 208 is a cylindrical member that is positioned at the proximal end of the insertion instrument 10. In some embodiments, the cap 208 comprises a series of alternating ridges 290 and valleys 291 (as shown in FIG. 6A) that advantageously provides a gripping surface for a user. The interior of the cap 208 can include a threaded surface (not shown) that can interact with a threaded surface that extends from the sleeve 250. The cap 208 can be configured to house a spring member 280 (shown in FIGS. 4B and 4C) that interacts with the pin actuator 210 to allow for controlled motion of the pin actuator 210.

The cap 208 also includes a delivery hole 295 located on a top surface of the cap 208 as shown in FIG. 6B. Spinal implants (e.g., spinal screws) and implantation tools (e.g., screw drivers) can be delivered down the delivery hole 295 through the lumen 240. The insertion instrument 200 is configured such that when a buttress plate 10 is connected to the distal portion 202 of the insertion instrument, the aperture of the buttress plate 10 will be aligned with all or part of the distal end of the lumen 240. The delivery hole 295 is advantageously configured such that spinal implants or tools delivered through the delivery hole 295 can be guided to a desired position. For example, the delivery hole 295 can be configured such that when a spinal screw 105 is inserted through the delivery hole 295, the spinal screw 105 is guided to the aperture 25 of the buttress plate 10, where it can then be screwed into a vertebral body using a screw driver also delivered through the delivery hole 295 of the cap.

The pin actuator 210 comprises a pin member that is operably connected to a proximal portion of the inner shaft 255. As shown in FIG. 6A, the pin actuator 210 can comprise one or more arms having a longitudinal axis that is perpendicular to the longitudinal axis of the sleeve 250. The pin actuator 210 is configured to be moveable (e.g., by a pulling or pushing force by a hand as in FIG. 6C), which also moves the inner shaft 255. In some embodiments, when the pin actuator 210 is pulled in a proximal direction, the inner shaft 255 is retracted. In some embodiments, the pin actuator 210 can go against a spring force generated by a spring member 280 when pulled in a proximal direction; removing the pulling force on the pin actuator 210 results in the pin actuator springing back to its original position (e.g., in extended mode). The pin actuator 210 is thus configured to assist in placing the inner shaft 255 in either its extended mode or retracted mode as discussed above, and can accommodate securing and/or decoupling of the buttress plate 10 to the insertion instrument 200.

When the buttress plate 10 is attached to the insertion instrument 200, the coupled elements can be delivered to a desired location in the body. The buttress plate 10 can be placed adjacent a spine, whereby a screw can be delivered through the insertion instrument 200 to secure the buttress plate 10 to a vertebral body.

Figure 7B:
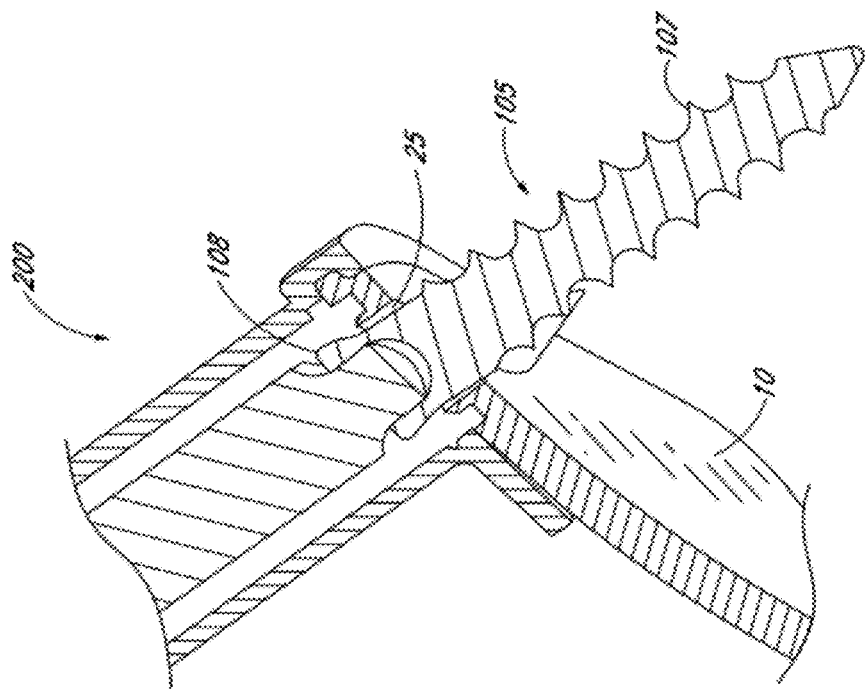
FIGS. 7A and 7B illustrate the interior of an insertion instrument during in use according to some embodiments of the present application.
Figure 7A:
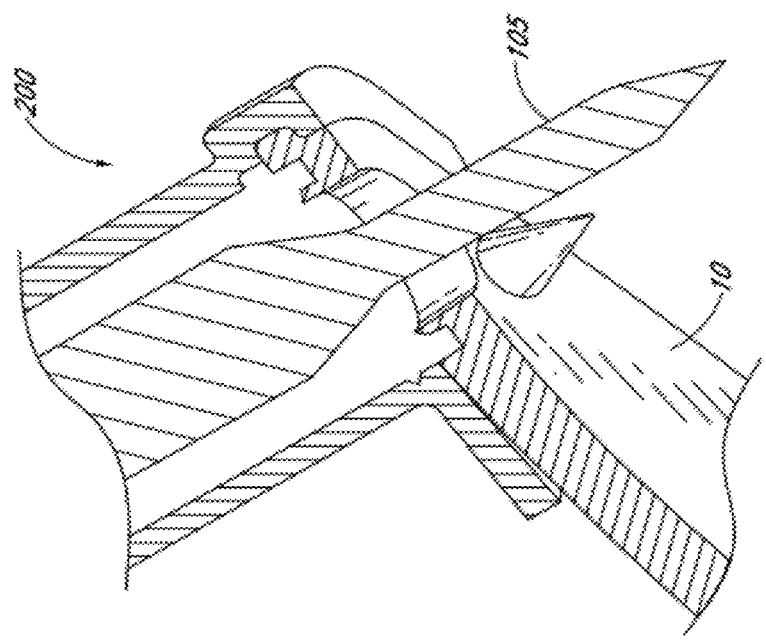

FIGS. 7A and 7B illustrate the interior of an insertion instrument during use according to embodiments of the present application. In particular, FIG. 7A illustrates the interior of the insertion instrument with a hole forming device therethrough, while FIG. 7B illustrates the interior of the insertion instrument with a screw therethrough.

FIG. 7A illustrates an interior of the insertion instrument 200 with a hole forming device 305 therethrough. The inner shaft 255 of the insertion instrument 200 has been removed for clarity. The hole forming device 305 is optional, and can comprise a shaft with a cutting end, bone awl, drill or other tool for forming a hole in one or more vertebrae. The hole-forming device can be part of a kit including the insertion instrument and buttress plate. The hole forming device 305 can pass through the aperture 25 of the buttress plate, and can be used prior to introducing the screw 105 so that the screw can be more easily introduced into the bone member.

FIG. 7B illustrates an interior of the insertion instrument 200 including a screw 105. The screw 105 includes a shaft 107 and head member 108 and can be delivered through the lumen 240 of the insertion instrument 200. The shaft 107 of the screw 105 can pass through the aperture 25 of the buttress plate 10, whereby the shaft is inserted into a vertebral body. Once the screw 105 is inserted into a vertebral body, thereby securing the buttress plate 10 to the vertebral body, the insertion instrument 200 can be decoupled from the screw 105 (e.g., by applying a pulling force on the pin actuator to retract the inner shaft 255). The insertion instrument 200 can then be removed from the body, while the buttress plate 10 is left in a desired location adjacent the spine. The buttress plate 10 can advantageously extend across an intervertebral space to block or inhibit an intervertebral spacer or cage from unintentionally backing out from the intervertebral space.

Methods of Using a Buttress Plate System

Methods of using a buttress plate system including an intervertebral spacer, buttress plate, spinal screw and insertion instrument will now be described.

Figure 8A:
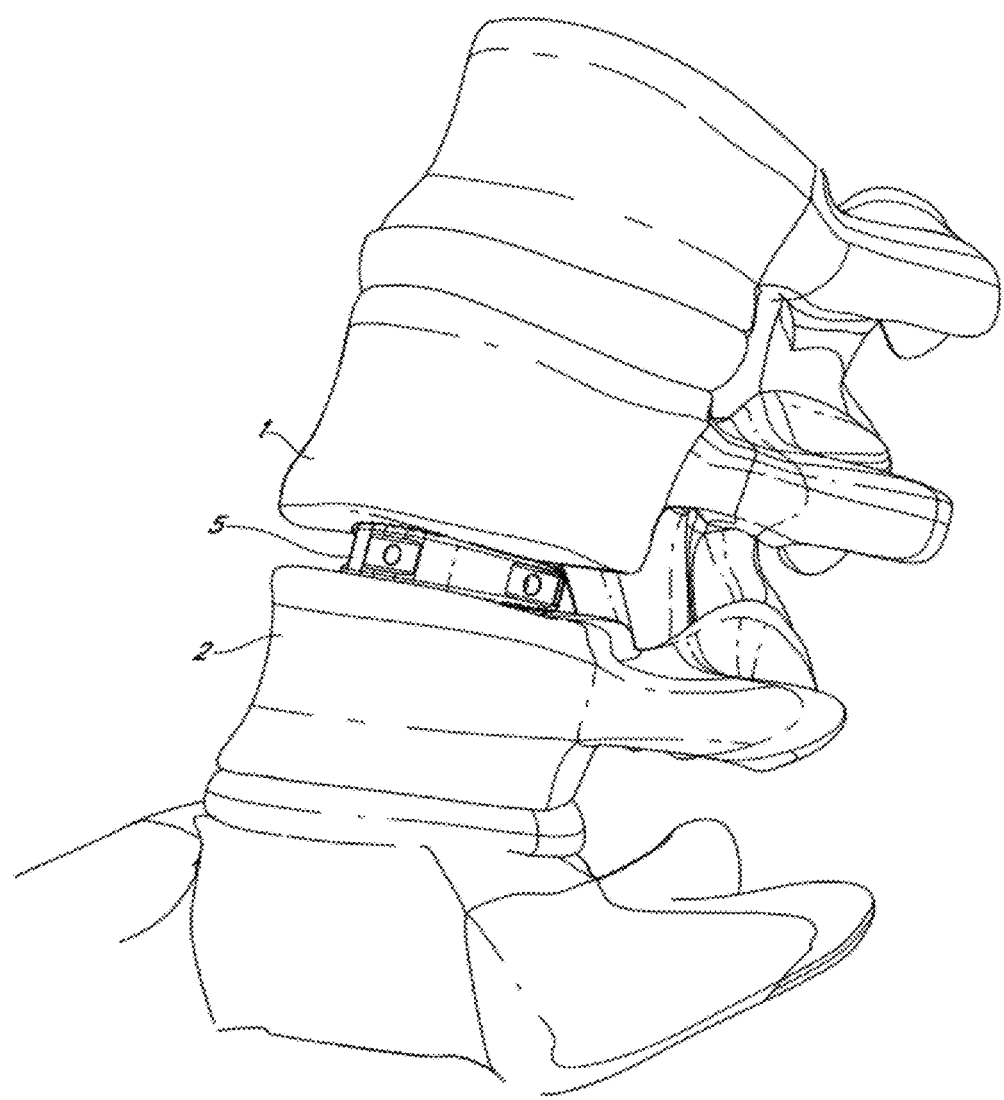
FIGS. 8A-8D illustrate steps in a method of using a buttress plate system according to some embodiments.
Figure 8B:
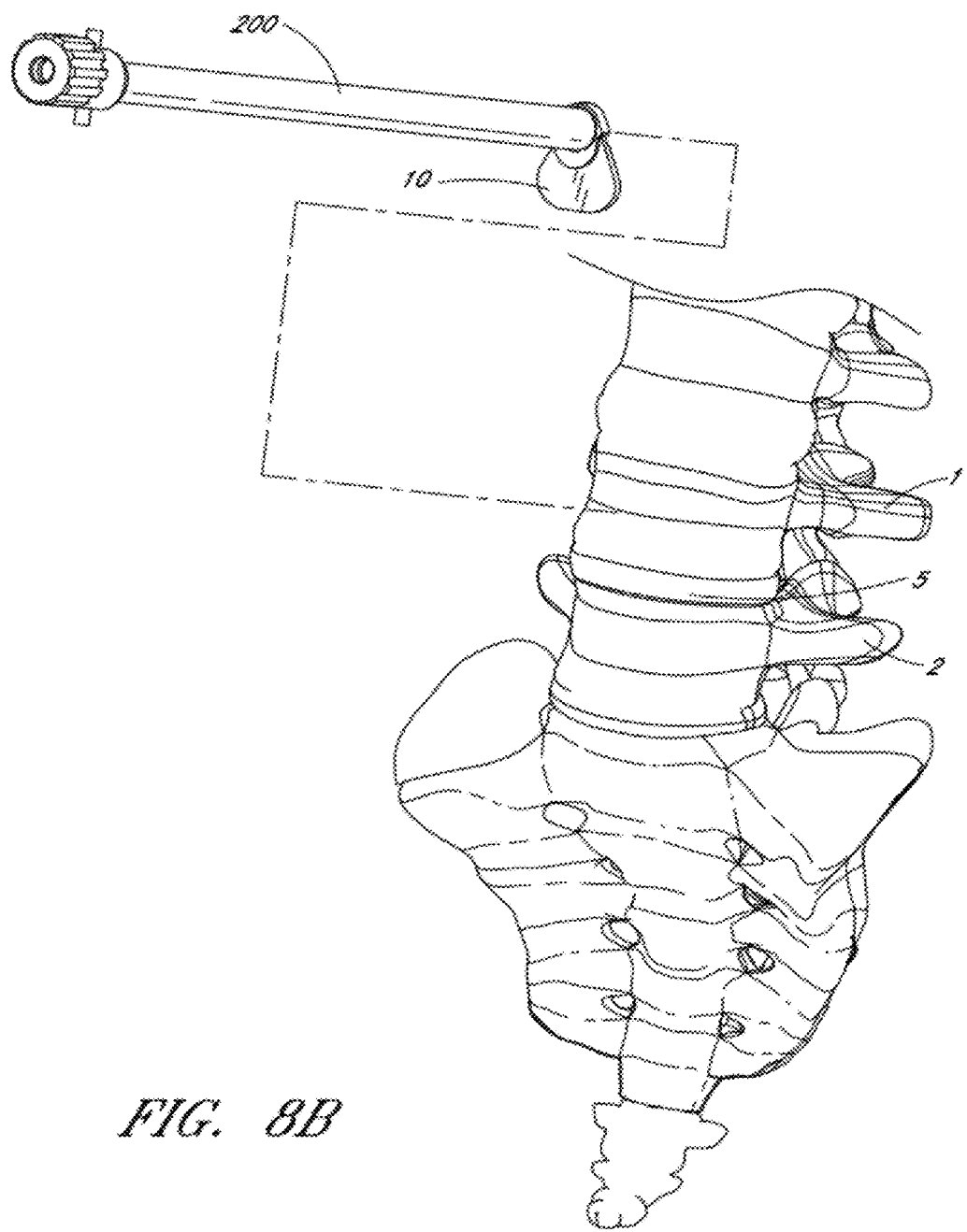
Figure 8C:
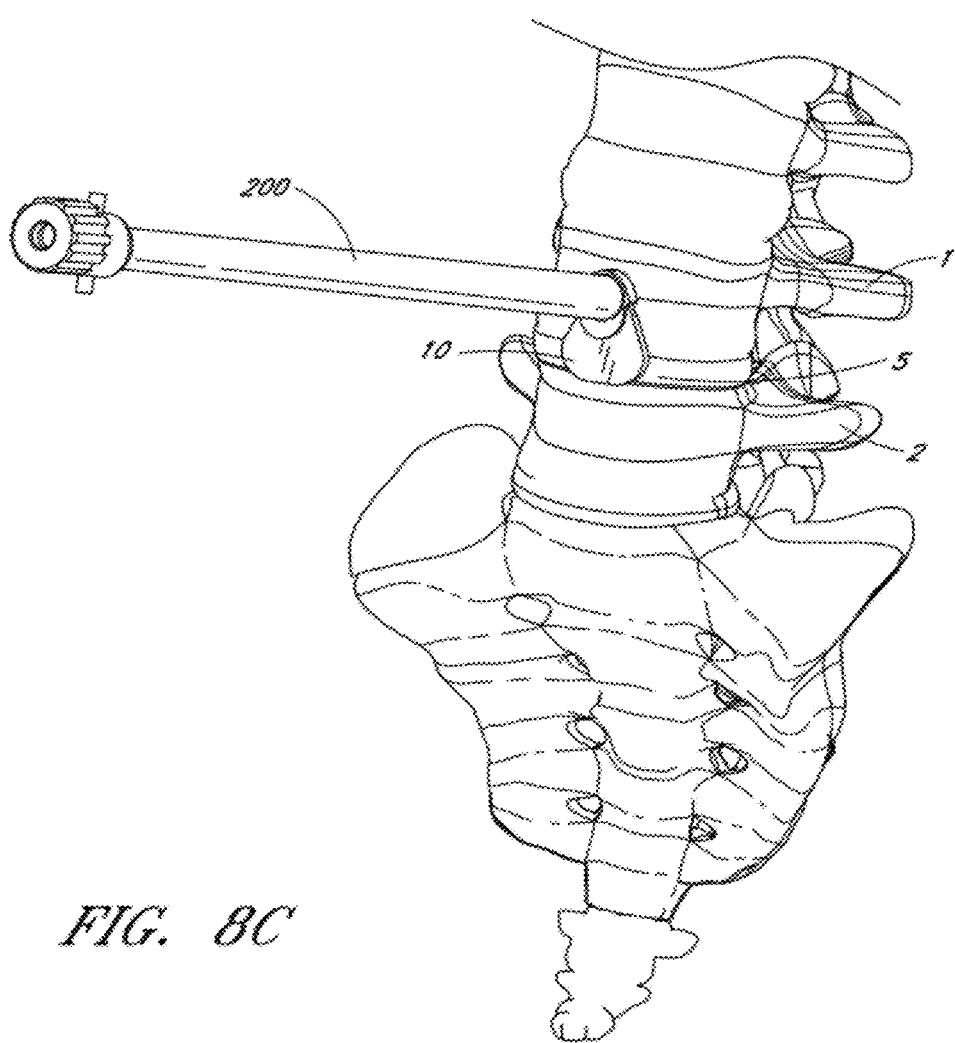
Figure 8D:
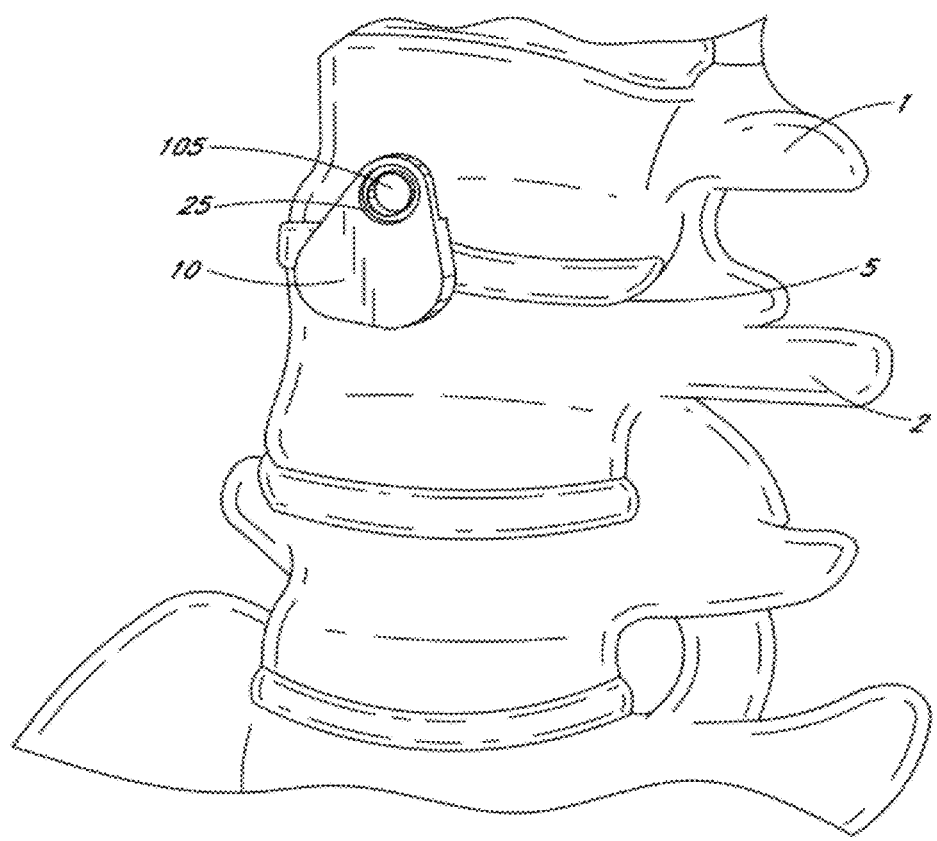

FIGS. 8A-8D illustrate steps in methods of using a buttress plate system according to some embodiments. FIG. 8A illustrates the step of inserting a spacer 5 into an intervertebral space between a first vertebra 1 and second vertebra 2. FIG. 8B illustrates the step of securing an insertion instrument 200 and buttress plate 10 prior to delivering the buttress plate 10 to a location adjacent the spine. FIG. 8C illustrates the step of using the insertion instrument 200 to deliver the buttress plate 10 to a location adjacent the spine. FIG. 8D illustrates the step of removing the insertion instrument 200 while leaving the buttress plate 10 fixed to the spine. More specific details regarding each of these steps is discussed below.

As shown in FIG. 8A, an intervertebral spacer 5 can be provided and inserted in an intervertebral space between a first vertebra 1 and a second vertebra 2, such as in the lumbar region. In other embodiments, a spacer can be provided in the cervical or thoracic region. To prevent or inhibit the intervertebral spacer 5 from unintentionally backing out of the intervertebral space, a buttress plate 10 can be provided that can be fixed to the first vertebra 1 and/or second vertebra 2. The buttress plate 10 comprises a plate body that can include any of the features described above, including a pair of engagement members (e.g., spikes) and an aperture for receiving a screw.

To direct the buttress plate 10 to a location adjacent the spine, an insertion instrument 200 (as discussed above) can be provided. The insertion instrument 200 can include a proximal portion, a distal portion, a sleeve and an inner shaft. The proximal portion includes a pin actuator and cap, while the distal portion includes a buttress end and receiver portion. In its normal state, the inner shaft of the insertion instrument 200 extends beyond a distal end of the sleeve. The inner shaft is operably connected to the pin actuator, which is capable of causing retraction of the inner shaft.

As shown in FIG. 8B, outside of the body, the buttress plate 10 can be coupled to the insertion instrument 200. To secure the buttress plate 10 to the insertion instrument 200, a force is applied to the pin actuator to retract the inner shaft. This helps provide a space at the distal portion of the insertion instrument in which the buttress plate 10 can be inserted. The buttress plate 10 is inserted into the insertion instrument 200 such that it rests against the buttress end and is received within the receiver portion. In some embodiments, the buttress plate 10 includes a recessed edge that is configured to be received in the receiver portion. Once the buttress plate 10 is inserted into the insertion instrument 200, the force on the pin actuator can be removed, and the inner shaft can re-extend onto the surface of the buttress plate 10. The buttress plate 10 is thereby secured between the inner shaft and distal portion of the insertion instrument 200, such that the buttress plate 10 is coupled to the insertion instrument 200.

As shown in FIG. 8C, with the buttress plate 10 coupled to the insertion instrument 200, the insertion instrument 200 can be used to guide the buttress plate 10 to a desired location adjacent the spine. In some embodiments, the insertion instrument 200 can be inserted through a surgical opening in a patient as part of an open or mini-open surgical procedure. In other embodiments, an access system, for example, a sleeve and/or dilator system can be used with the insertion instrument to deliver the buttress plate to a desired location. In other embodiments, the insertion instrument 200 can be used on its own (e.g., as part of a mini-open surgery) without a sleeve or dilator to deliver the buttress plate 10 to a desired location.

Once the buttress plate 10 is delivered to a desired location adjacent the spine, the engagement members can be placed in contact with a vertebral body. The engagement members, which can include spikes, can dig or grip onto the surface the vertebral body, thereby providing an anchoring mechanism even before the buttress plate is secured to the vertebral body. The engagement members help to stabilize the position of the buttress plate 10 relative to the spine prior to using a screw 105 to secure the buttress plate 10 to the spine. After insertion of the screw 105, engagement members can limit and/or prevent rotational movement of the plate about the screw 105.

With the buttress plate 10 in place and properly stabilized, a spinal screw 105 can be delivered through the insertion instrument 200. The spinal screw 105 can be provided through a delivery hole in the cap of the insertion instrument and can be guided down the insertion instrument 200 directly towards the aperture of the buttress plate 10. A screw driver can then be delivered through the delivery hole of the insertion instrument 200 to rotate the spinal screw head, thereby driving the shaft of the spinal screw 105 into a vertebral body to secure the buttress plate 10 to the spine.

As shown in FIG. 8D, once the buttress plate 10 is secured to the spine, the insertion instrument 200 can be decoupled from the buttress plate 10. To decouple the insertion instrument 200 from the buttress plate 10, a force can be applied to the pin actuator to once again retract the inner shaft, thereby removing the compressive force on the buttress plate 10. The insertion instrument 200 can then be removed away from the buttress plate 10 and out of the body. The buttress plate 10 remains secured to the spine and extends across at least a part of an intervertebral space, thereby helping to prevent or inhibit unintended back out of the intervertebral spacer 5.

It will be apparent to those skilled in the art that various modifications and variations can be made in the present embodiments without departing from the scope or spirit of the advantages of the present application. Thus, it is intended that the present application cover the modifications and variations of these embodiments and their equivalents.

What is claimed is:

1. A spinal implant system comprising:
   an intervertebral spacer configured and arranged to be positioned in an intervertebral space between a first vertebra and a second vertebra of a patient;
   a buttress plate having a plate body configured and arranged to extend across at least a portion of the intervertebral space to at least inhibit the intervertebral spacer from backing out from the intervertebral space when the buttress plate is connected to at least one vertebra, the buttress plate including a top surface and a bottom surface, wherein the bottom surface includes at least one engagement member and a recessed edge and the top surface includes a groove, the buttress plate further comprising a single aperture that extends through the top surface and bottom surface, and the buttress plate comprising generally triangular plate body having three sides meeting at three rounded corners, wherein the recessed edge extends across an apex portion of the plate body;
   a single screw configured to be inserted through the aperture of the buttress plate and into a single vertebra to connect the buttress plate to the vertebra; and
   an insertion instrument having a proximal portion, a distal portion, and a sleeve there between comprising a lumen, the insertion instrument further comprising an inner shaft having length defined between a proximal end and a distal end and having a lumen, wherein a majority of the length of the inner shaft is configured to be disposed within the lumen of the sleeve, wherein the proximal portion includes a cap including a delivery hole and a pin actuator for controlling retraction of the inner shaft within the sleeve, and wherein a distal portion of the sleeve includes a receiver portion configured to receive the buttress plate, wherein the receiver portion comprises a recess configured to receive the recessed edge of the bottom surface of the buttress plate, wherein the distal end of the inner shaft is configured to engage the groove of the top surface of the buttress plate, wherein the insertion instrument comprises a spring member configured to force the inner shaft into the groove on the top surface of the buttress plate in an engaged configuration, and wherein the insertion instrument is configured to couple to the buttress plate in the engaged configuration, the insertion instrument is configured to deliver the buttress plate to an implantation site in the engaged configuration such that the at least one engagement member on the bottom surface of the buttress plate engages at least one vertebra, and the insertion instrument is configured to guide the screw through the lumen to the aperture of the buttress plate in the engaged configuration.

2. The system of claim 1, wherein the buttress plate comprises a pair of engagement members for engaging at least one vertebra, wherein the pair of engagement members comprise a pair of spikes.

3. A spinal implant system consisting essentially of:
a buttress plate consisting essentially of a plate body having a top surface, a bottom surface, and a single aperture extending therethrough, wherein the top surface is configured to face away from a vertebral body upon implantation, the bottom surface is configured to face toward a vertebral body upon implantation, and the aperture is configured to receive a single screw, wherein the top surface has a groove around the aperture and the bottom surface has a recessed edge, wherein the plate body is configured and arranged to extend across at least a portion of the intervertebral space and at least inhibit an intervertebral spacer from backing out when the buttress plate is connected to a single vertebrae; and an insertion instrument comprising a proximal portion, a distal portion, a sleeve there between comprising a lumen, and an inner shaft having length defined between a proximal end and a distal end, wherein a majority of the length of the inner shaft is configured to be moveably disposed within the lumen of the sleeve, wherein a distal portion of the sleeve comprises a receiver portion having a recess configured to receive the recessed edge of the bottom surface of the buttress plate, wherein the distal end of the inner shaft is configured to engage the groove of the top surface of the buttress plate, and wherein the insertion instrument is configured to deliver the buttress plate to an implantation site and guide the screw through the sleeve to the aperture of the buttress plate when the buttress plate is coupled to the insertion instrument and the bottom surface of the buttress plate faces toward the implantation site.

4. The system of claim 3, wherein the buttress plate comprises a curved plate body.

5. The system of claim 3, wherein the buttress plate comprises a generally triangular plate body having three sides meeting at three rounded corners.

6. The system of claim 3, wherein the buttress plate comprises a pair of engagement members for engaging at least one vertebra.

7. The system of claim 6, wherein the engagement members comprise a pair of spikes.

8. The system of claim 3, wherein the proximal portion of the insertion instrument includes a cap having a delivery hole through which the screw can be delivered.

9. The system of claim 3, wherein the insertion instrument comprises a spring member configured to force the inner shaft into the groove on the top surface of the buttress plate in an engaged configuration.

10. The system of claim 9, wherein the insertion instrument comprises a pin actuator operably coupled to the inner shaft, wherein the pin actuator controls retraction of the inner shaft.

11. The system of claim 10, wherein the insertion instrument is configured to be coupled to the buttress plate when the pin actuator is in a neutral position.

12. The system of claim 11, wherein the insertion instrument is configured to release the buttress plate when the pin actuator is retracted.

13. A spinal implant system comprising:
a buttress plate comprising a plate body configured to extend across at least a portion of the intervertebral space and at least inhibit an intervertebral spacer from backing out when the buttress plate is connected to at least one vertebra, the buttress plate including an aperture for receiving a screw, the buttress plate comprising a top surface and a bottom surface, wherein the top surface is configured to face away from a vertebral body upon implantation, and the bottom surface is configured to face toward a vertebral body upon implantation, the top surface comprising a groove around the aperture and the bottom surface comprising a recessed edge, and the buttress plate comprising a generally triangular plate body having three sides meeting at three rounded corners, wherein the recessed edge extends across an apex portion of the plate body; and an insertion instrument comprising a proximal portion, a distal portion, a sleeve there between, and an inner shaft having a length defined between a proximal end and a distal end, wherein a distal portion of the sleeve comprises a receiver portion configured to couple to the buttress plate, wherein the receiver portion comprises a curvilinear member having a recess formed therein configured to engage the recessed edge of the bottom surface of the buttress plate; and wherein the distal end of the inner shaft is configured to engage the groove of the top surface of the buttress plate and a majority of the length of the inner shaft is configured to be disposed within a lumen defined in the sleeve, and wherein the insertion instrument is configured to deliver the buttress plate to an implantation site with the bottom surface of the buttress plate facing the implantation site and to guide the screw through the lumen within the sleeve to the aperture of the buttress plate when the buttress plate is coupled to the insertion instrument.

14. The system of claim 13, wherein the inner shaft is positioned coaxially within the sleeve.

15. The system of claim 13, wherein the insertion instrument is configured to clamp the buttress plate between the distal end of the inner shaft and the receiver portion of the sleeve.

16. The system of claim 13, wherein the insertion instrument couples directly with the buttress plate.

17. The system of claim 13, wherein the buttress plate has a stele aperture configured to accept a single screw, wherein the single screw engages a single vertebra.

18. The system of claim 13, further comprising an intervertebral spacer configured and arranged to be positioned in an intervertebral space between a first vertebra and a second vertebra.

19. The system of claim 13, wherein the distal portion of the insertion instrument is configured to couple with the buttress plate via a top surface of the buttress plate and a recessed edge in the bottom surface of the buttress plate such that no portion of the insertion instrument extends distally beyond the bottom surface of the buttress plate in the engaged configuration.

* * * * *

UNITED STATES PATENT AND TRADEMARK OFFICE
CERTIFICATE OF CORRECTION

PATENT NO. : 8,998,988 B2
APPLICATION NO. : 12/981193
DATED : April 7, 2015
INVENTOR(S) : James Milton Phillips and Robbie Dale Dickerman It is certified that error appears in the above-identified patent and that said Letters Patent is hereby corrected as shown below:

In the claims

Claim 1, Column 10, Line 58, change "comprising" to --comprising a--.
Claim 17, Column 13, Line 2, change "stele" to --single--.

Signed and Sealed this
Third Day of May, 2016

Michelle K. Lee
*Director of the United States Patent and Trademark Office*